United States Patent [19]

Hamasaki et al.

[11] Patent Number: 5,272,092
[45] Date of Patent: Dec. 21, 1993

[54] METHOD FOR ANALYZING A REACTION SOLUTION

[75] Inventors: Fumitoshi Hamasaki; Hajime Betsui; Kyoko Imai; Hiroshi Umetsu, all of Katsuta, Japan

[73] Assignee: Hitachi, Ltd., Tokyo, Japan

[21] Appl. No.: 793,650

[22] Filed: Nov. 18, 1991

Related U.S. Application Data

[62] Division of Ser. No. 268,587, Nov. 8, 1988, abandoned.

[30] Foreign Application Priority Data

Nov. 12, 1987 [JP] Japan .................. 62-286168
Aug. 26, 1988 [JP] Japan .................. 63-210740

[51] Int. Cl.$^5$ .................. B01F 3/08; G01N 21/76
[52] U.S. Cl. .................. 436/172; 422/64;
422/65; 422/67; 73/64.41; 73/64.42; 73/64.43;
73/64.1; 366/273; 366/116
[58] Field of Search .................. 422/64, 58, 65, 102,
422/67.73, 52; 436/172. 531, 807, 808; 73/64.1;
366/273, 116

[56] References Cited

U.S. PATENT DOCUMENTS

| | | | |
|---|---|---|---|
| 3,623,844 | 1/1972 | Anthon | 422/64 |
| 3,645,506 | 2/1972 | Selesnick | 23/108 |
| 4,102,649 | 7/1978 | Sasaki | 23/259 |
| 4,202,634 | 5/1980 | Kraft et al. | 366/116 |
| 4,227,815 | 10/1980 | Hoffa | 366/273 |
| 4,313,735 | 2/1982 | Yamashita et al. | 422/64 |
| 4,457,893 | 7/1984 | Takekawa et al. | 422/64 |
| 4,540,549 | 9/1985 | Manabe | 422/64 |
| 4,778,763 | 10/1988 | Makiguchi et al. | 422/64 |
| 4,793,973 | 12/1988 | Ringrose | 422/102 |
| 4,871,683 | 10/1989 | Harris et al. | 422/64 |
| 4,876,069 | 10/1989 | Jochimsen | 366/273 |

FOREIGN PATENT DOCUMENTS 42325 3/1982 Japan .

Primary Examiner—James C. Housel
Assistant Examiner—Ramon Torres
Attorney, Agent, or Firm—Fay, Sharpe, Beall, Fagan, Minnich & McKee

[57] ABSTRACT

A plurality of reaction containers each being charged with an agitation ball made of a magnetic material are circularly arranged on a reaction disk so as to be supplied with a reagent and a sample. The reaction disk is driven reciprocatingly at a small amplitude for a predetermined time so as to cause the reaction containers to be vibrated arcuately each time a new reaction container is supplied with the reagent. As a result of the vibration of the reaction containers, the agitation balls in the respective reaction containers vigorously move to agitate the reaction solutions in the respective reaction containers. A photometric device is disposed so as to apply a light to the reaction container thereby to allow a fluorescent or absorbance photometric measurement. In the reaction container brought to the photometric measuring position, the agitation ball is attracted to the wall of the reaction container so as to be kept away from the path of light in the photometric device.

22 Claims, 8 Drawing Sheets

METHOD FOR ANALYZING A REACTION SOLUTION

This is a divisional application of Ser. No. 07/268,587, filed Nov. 8, 1988, now abandoned.

BACKGROUND OF THE INVENTION

The present invention relates to an analyzing apparatus capable of agitating a reaction solution and, more particularly, to an analyzing apparatus having a function for agitating a mixture of a sample and a reagent in a reaction container.

Conventionally, analyzing apparatus having an agitating function are so arranged that a plurality of reaction containers are successively brought to a stirring position and the contents of the successive reaction containers are agitated by the same agitating bar. An example of such analyzing apparatus is disclosed in Japanese Patent Laid-Open Publication No. 57-82769. With this arrangement, the analysis is unfavorably affected by carry-over of the reaction solutions which inevitably takes place due to the common use of the same agitating bar. In order to obviate this problem, attempts have been made for agitating the reaction solutions in a non-contacting manner. Japanese Patent Laid-Open No. 57-42325 discloses an analyzing apparatus in which a disk is disposed on the radially inner side of a circumferential row of a plurality of reaction containers arranged on a turn table such that the disk contacts the wall of the reaction containers. The reaction containers are rotated as the disk is rotated reciprocatingly. This arrangement does not employ an agitating bar.

Japanese Patent Laid-Open Publication No. 52-143551 discloses an agitating system, though this system is not provided with an analyzing function. This system has a multiplicity of dilution chambers arranged in X- and Y-directions on a rectangular plastic plate and the solutions in the chambers are agitated as the plate is vibrated in the X-direction. Since the agitation cannot be effected satisfactorily by mere vibration alone, the plate is supported at its one end by posts and a solenoid is used to impart an arcuate motion to the plate.

Japanese Patent Laid-Open Publication No. 61-56972 discloses a spectrophotometer in which a cell holder on which a multiplicity of sample cells are set is moved linearly so as to bring the cells to a measuring position successively and then the cell holder is moved backward. In this spectrophotometer, forward and rearward driving signals are alternately delivered to the cell holder so as to shake the sample cells forwardly and backwardly thereby to agitate the samples.

In general, an automatic analyzing system is required to efficiently handle a multiplicity of samples so that the agitation is to be effected in a short time without carry-over of the reaction solutions.

The analyzing apparatus disclosed in Japanese Patent Laid-Open Publication No. 57-42325 mentioned before can agitate the reaction solutions by causing the reaction containers to rotate about their axes. This, however, requires a complicated mechanism for driving the reaction containers. In the apparatus shown in Japanese Patent Laid-Open Publication No. 52-143551, samples are agitated by an agitation bar which is used commonly for the successive chambers so that carry-over contamination of samples is inevitably caused to deteriorate the accuracy of the analysis.

The apparatus shown in Japanese Patent Laid-Open Publication No. 61-56972 requires a considerably long agitation time because the agitation is effected by a mere oscillation of rectangular cells back and forth.

SUMMARY OF THE INVENTION

Accordingly, an object of the present invention is to provide an automatic analyzing apparatus which is capable of efficiently agitating solutions in the reaction containers by a simple arrangement.

Another object of the present invention is to provide an automatic analyzing apparatus which is capable of repeatedly effecting agitation of reaction solution in the period from the supply of a sample and a reagent until the measurement of the reaction solution, so as to promote the reaction between the sample and the reagent.

Still another object of the present invention is to provide an automatic analyzing apparatus which is capable of effecting agitation of the reaction solution without any risk of contamination due to carry-over.

A further object of the present invention is to provide a reaction container which can enhance the effect of agitation of a reaction solution and which is readily handled.

According to the invention, there is provided an automatic analyzing apparatus having a plurality of reaction containers arranged on a reaction disk. The reaction disk is arcuately and vibratingly driven so that an agitation member is moved within the reaction container so as to agitate the solution in the reaction container.

When the reaction disk is arcuately and vibratingly driven under an appropriate condition, kinetic energy is imparted to the agitation member which is dipped in the reaction solution in each of the reaction containers carried by the reaction disk. In consequence, the agitation member tends to move within the agitation container. However, since the movement of the agitation member is limited by the wall of the reaction container, the member revolves within the reaction container to thereby agitate the solution in the container.

In a preferred form of the present invention, the reaction disk is vibratingly driven at a high frequency of 10 to 40 Hz at an amplitude of 0.8 to 3.0 mm so as to attain a high efficiency of agitation. Agitation is effected satisfactorily without troubles such as splashing of the solution out of the container when the diameter of the agitation member is not greater than a half of the inside diameter of the reaction container while the specific gravity of the agitation member is 4 times or more as large as that of the solution to be agitated. It will be understood that contamination of reaction solutions via the agitation member does not take place because each reaction container has its own agitation member.

When the apparatus of the present invention is actually carried out as an automatic analyzing apparatus, it is necessary that a high degree of photometric accuracy is achieved. To this end, the reaction container having a curved inner surface can be provided with a pair of smooth light-transmitting windows. With such an arrangement, photometric operation is performed stably regardless of any slight offset of the reaction container with respect to the optical path of the photometer, without impairing the revolution of the agitation member. The agitation member may be made of a ferromagnetic material so that it is magnetically attracted by a magnet disposed in the vicinity of the photometric position to prevent the agitation member from interrupting the path of the photometric light at the time of photometry.

According to the invention, the vibrating movement of the reaction disk causes vibration of all the reaction containers carried by the disk. Since this vibration is effected each time a new reaction container is supplied with sample and reagent, each container is frequently vibrated during a period from reaction commencement to the photometric measurement. When an insoluble reagent having a specific gravity different from the solution is contained in the reaction container, the reaction is promoted by this repetitive agitation.

DESCRIPTION OF THE PREFERRED EMBODIMENTS

An embodiment of the present invention will be described with reference to FIGS. 1 to 4.

A plurality of reaction containers 2 are arranged on a rotary reaction disk 1 along a peripheral region of the disk 1. The reaction disk is driven rotationally by a driving device 3. The driving device 3 is capable of operating in different modes: namely, a mode in which it drives the reaction disk 1 intermittently by a distance of the pitch or separation between adjacent containers and a mode in which it reciprocatingly drives the reaction disk in a short time. In the latter mode, the reaction disk 1 is driven reciprocatingly at high speed with a very small amplitude in a vibratory manner so that the solutions in the reaction containers are agitated.

Figure 3:
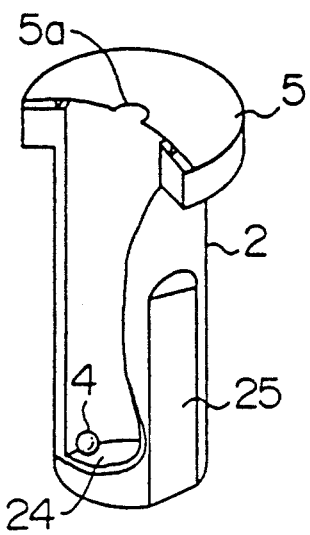
FIG. 3 is a partly cut-away sectional view of a reaction container suitable for use in fluorescent photometry.

Each of the reaction containers 2 carried by the reaction disk 1 is beforehand charged with a ball-like agitation member (referred to as an "agitation ball" hereinafter) 4 which is made of permalloy. In this embodiment, reaction containers designed for fluorescent photometry are used as shown in FIG. 3. Each reaction container is closed at its top end by an aluminum membrane 5 so as to prevent the agitation ball 4 from coming off the reaction container 2 during transportation. This reaction container 2 has a cylindrical body which is 6.2 mm in inside diameter and 30 mm in depth, with a flat incident window 24 provided in the bottom thereof and a flat emanating window 25 in the side wall thereof. The body of the reaction container 2 is made of a light-transmitting material such as a glass or an acrylic resin. The arrangement is such that, when the reaction container is set on the reaction disk 1, an aperture 5a of a predetermined size is formed in the seal membrane 5 by means of a seal breaker which is not shown, so that pipetting of a sample and/or reagent which is to be conducted by means of a probe 15 of a pipetting device 14 can be executed without being interfered by the seal membrane 5.

Figure 2:
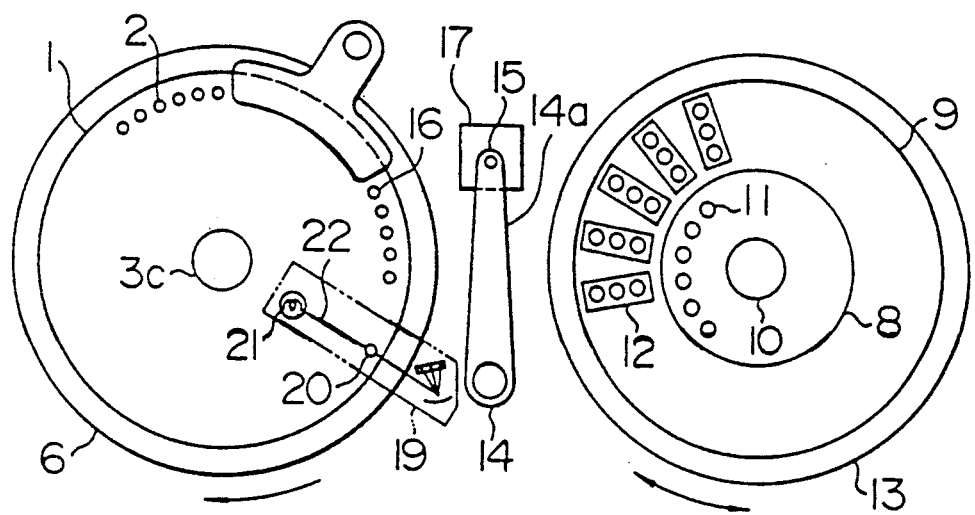
FIG. 2 is a schematic plan view of the embodiment.

A reaction thermostat tank 6 has a permanent magnet or a solenoid 7 which is located in the vicinity of a position where photometry is conducted by a photometer 19, as shown in FIG. 2. The permanent magnet or the solenoid 7 is capable of magnetically attracting the agitation ball 4 to a position opposite to the emanating window 25 in the reaction container 2 which has been brought to the photometric position, so that the agitation ball 4 never interrupts the path of light beam 22 during the photometric measurement.

The apparatus also has a rotary sample disk 8 and a rotary reagent disk 9 which are arranged concentrically with each other. These disks 8 and 9 are carried by a central drive shaft 10 so that they are rotatable about the axis of the drive shaft 10 as a unit with each other. Although in the illustrated arrangement the sample disk 8 is disposed on the radially inner side of the reagent disk 9, this is only illustrative and the arrangement may be such that the sample disk 8 is disposed on the radially outer side of the reagent disk 9. The sample disk 8 carries a plurality of sample cups 11, while the reagent disk 9 carries a plurality of groups of reagent cups 12 each group having a plurality of reagent cups containing different reagents.

More specifically, each group of the reagent cups includes cups 12 of a first reagent and of a second reagent which are used for a specific item of the analytical measurement. The drive shaft 10 is intermittently rotatable so that the reagent disk 9 and the sample disk 8 are rotated about the axis of the drive shaft 10 through an angle corresponding to the pitch of the arrangement of the reagent cups 12 and the sample cups 11 or a multiple of the pitch. The reagent cups 12 and the sample cups 11 are set on the respective disks replaceably so that they can be changed in accordance with the object of the examination. The sample cups 11 are arranged in a sample thermostat tank so as to be maintained at a predetermined temperature. Similarly, the reagent cups 12 are disposed in a reagent cold preserving tank 13 so as to be maintained at a predetermined temperature. The apparatus further has a pipetting device 14 for pipetting the aforementioned samples or a reference sample or the reagent from the sample cups 11 or from the reagent cups 12 to the reaction containers 2. The pipetting device 14 has a rotatable arm 14a and a pipetting probe 15 provided on the end of the arm 14a. In operation, the probe 15 sucks a sample or reagent and is moved by the rotatable motion of the arm 14a to a sample and reagent pipetting position 16 where one of the reaction containers 2 is disposed. The pipetting probe 15 then discharges the sample or the reagent into the reaction container 2. The sample disk 8 or the reagent disk 9 are moved by a drive shaft 10 to and stopped at a position where the sample cup 11 or the reagent cup 12 is disposed in the path of movement of the probe 15. The apparatus further has a probe washing device 17 which is capable of supplying washing water to the outer and inner surfaces of the probe 15 thereby to wash the probe 15 sufficiently.

In operation, a predetermined amount of sample is sucked and metered by the probe 15 of the pipetting device 14 from one of the sample cups 11 on the sample disk 8, and the probe 15 then discharges the sample to one of the reaction container 2 at a designated position on the reaction disk 1. After the discharge of the sample, the probe 15 of the pipetting device 14 is sufficiently washed with water so as to prevent contamination of the next sample which contamination may otherwise be caused due to carry-over of the sample. Then, the reaction disk 1 is reciprocatingly and vibratingly driven by the high-speed reciprocatory driving device 3 at a frequency of 33 Hz and an amplitude of 1.2 mm for a period of 3 seconds. After the vibration, the reaction disk 1 is driven clockwise through an angle corresponding to the pitch of the reaction containers.

Figure 1:
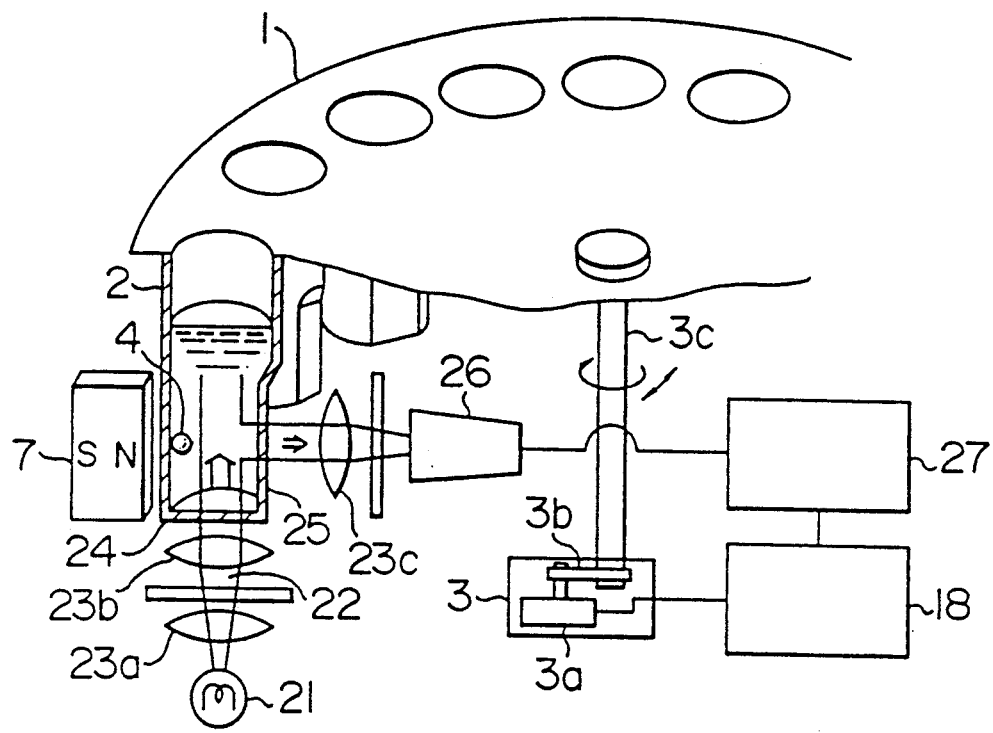
FIG. 1 is a schematic illustration of an essential portion of an embodiment of the analyzing apparatus shown in FIG. 2.

The high-speed reciprocating driving device 3 has, as shown in FIG. 1, a stepping motor 3a as a driving power source. The output shaft of the stepping motor 3a is connected to the shaft 3c carrying the reaction disk 1 through gears or a connection belt 3b. Obviously, the arrangement may be such that the shaft of the stepping motor 3a and the shaft 3c of the reaction disk are constructed as a unit with each other. In such a case, the power of the stepping motor 3a is transmitted to the reaction disk 1 directly without necessitating any intermediary such as a gear or a belt. The stepping motor 3a operates under the control of a central processing unit 18. The central processing unit 18 causes the stepping motor 3a to rotatively step at a rate of 5 pulses both in the forward direction and in the backward direction per 30 milli-sec for a period of 3 seconds. As a consequence, the reaction disk is made to vibrate at a frequency of about 33 Hz as mentioned above. This causes the reaction containers to vibrate at a frequency of about 33 Hz and with an amplitude on the order of several millimeters when the reaction disk has a diameter of about 300 mm, though the amplitude depends on factors such as the gear ratio. The high-speed reciprocating driving device 3 also serves as an intermittent driving means for effecting stepwise indexing rotation of the reaction disk so as to bring the successive reaction containers 2 to the designated position.

Meanwhile, the sample disk 8 is rotated so as to bring the next sample cup to the pipetting position. This operation is conducted cyclically and repeatedly so that the samples of a predetermined number are transferred to the respective reaction containers.

A similar operation is executed for the reagent. Namely, the from one of the successive reagent cups 12 is withdrawn by the pipetting device 14 and is discharged into one of the reaction containers 12 which are successively brought to the pipetting position 16. After the delivery of the reagents each reaction container 2, the reaction disk 1 is rotated reciprocatingly for 3 seconds by the high-speed reciprocating driving device 3 so as to effect agitation of the reaction solution in the reaction container 2. Then, the reaction disk 1 is rotatively moved through the angle corresponding to the pitch of the arrangement of the reaction containers 2 thereby to bring the next reaction container 2 to the pipetting position. The transfer of the reagents is commenced with the first reagent followed by the transfer of the second reagent. Thus, the reaction disk 1 is rotated in an indexing manner so that the reaction containers 2 are charged with the samples and the reagents. The sample is typically a liquid extracted from living bodies, e.g., blood serums, plasmas and urine. The reagents used in this system may be one of many reagents which are ordinarily used in medical examinations for the analyzing above-mentioned type of samples.

The sample and the reagent which have been charged into each reaction container react with each other within the reaction container 2. For instance, assuming that the one-pitch feed of the reaction containers takes place in a period of 18 seconds and that the reciprocating driving of the reaction disk 1 is conducted for a period of 3 seconds, all the reaction containers 2 on the reaction disk repeatedly undergo a 3-second vibration per an interval of 18 seconds. As a consequence, the reaction solutions in all the reaction containers 2 are subjected repeatedly to 3-second agitation per interval of 18 seconds during all courses of reaction. The reaction containers 2 with their contents thus agitated are successively brought back to the pipetting position 16 where a coloring reagent is added to the contents, i.e., the reaction solutions, of the successive reaction containers, whereby a coloring reaction takes place and proceeds in each reaction container 2.

The photometer 19 used in this embodiment is a multi-wavelength simultaneous measurement type device having a plurality of detectors. The photometer 19 is disposed on the photometric measurement position 20 so as to oppose one of the reaction containers 2. Thus, the reaction container 2 which is passing through the photometric measurement position 20 renders a light beam 22 from a light source lamp 21 to pass the container and to reach the photometer 19.

Referring back to FIG. 1, the light from the light source lamp 21 is condensed by lenses 23a and 23b and the thus condensed light is made to impinge upon the reaction solution as an exciting light through the incidence window 24 provided in the bottom of the reaction container 2.

The fluorescent light emitted from the reaction solution passes through the emanating window 25 of the reaction container and is received through a lens 23c by a photo-multiplier 26 which is capable of detecting the fluorescent light intensity. As the reaction disk 1 is rotated intermittently, the successive reaction containers are brought to the photometric measuring position 20 so that the fluorescent light intensities of the respective reaction solutions are measured. The outputs from the photometer 19 are delivered to a multiplexer which selects signals of the wavelengths of interest and the successive signals are input through the A/D converter 27 into the central processing unit 18 and are stored in a RAM annexed to the central processing unit 18.

Figure 4:
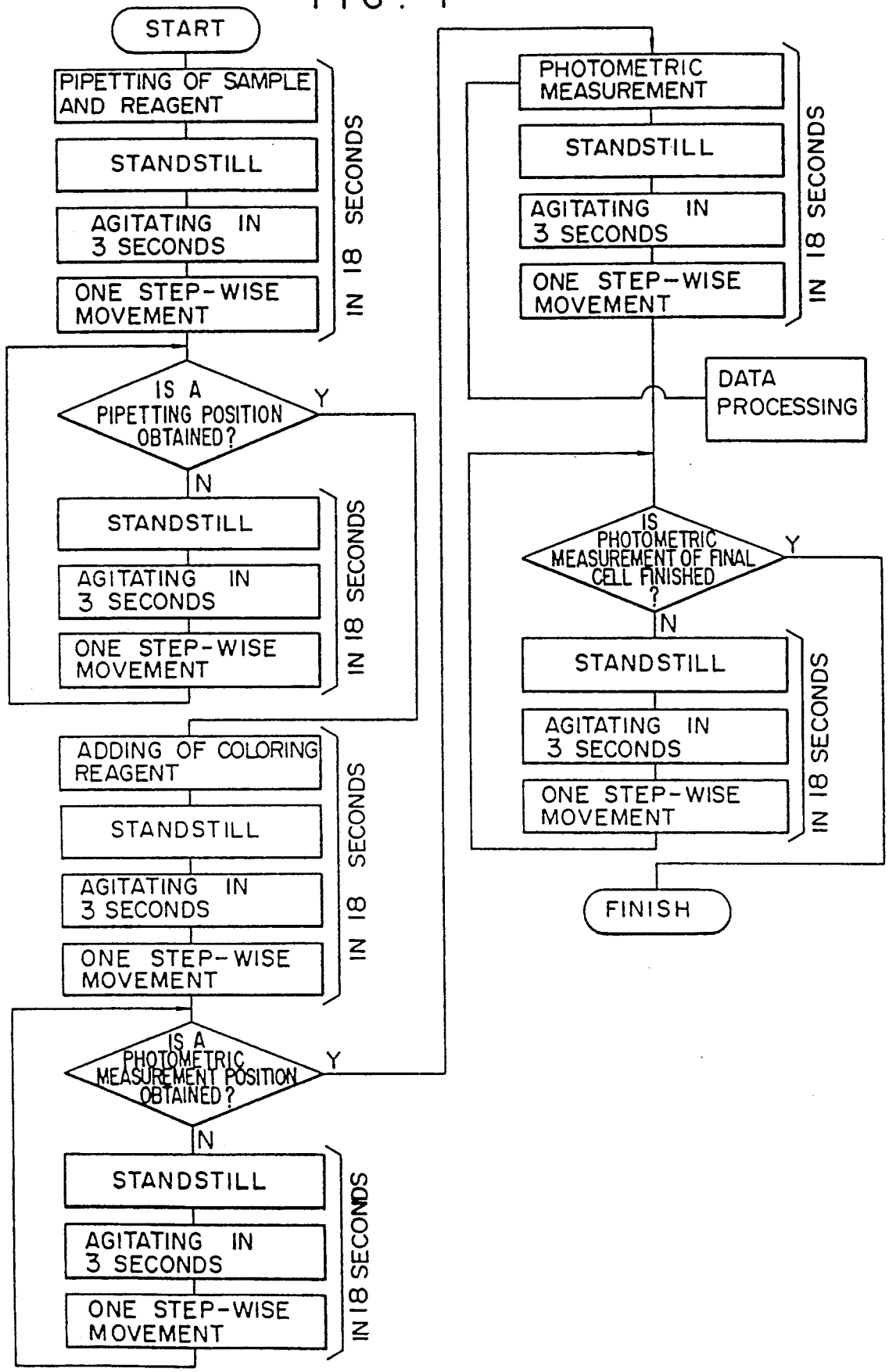
FIG. 4 is a flow chart illustrating the measuring process of the embodiment.

FIG. 4 shows a flow chart of a series of operations from the transfer of the sample and reagent until the end of the measurement including the agitation of the reaction solutions by the high-speed reciprocating driving of the reaction disk.

The central processing unit 18 conducts the control of the whole apparatus including the mechanical systems, as well as all the necessary data processing operations including computation of densities. The central processing unit 18 may be composed of a microcomputer.

Figure 5:
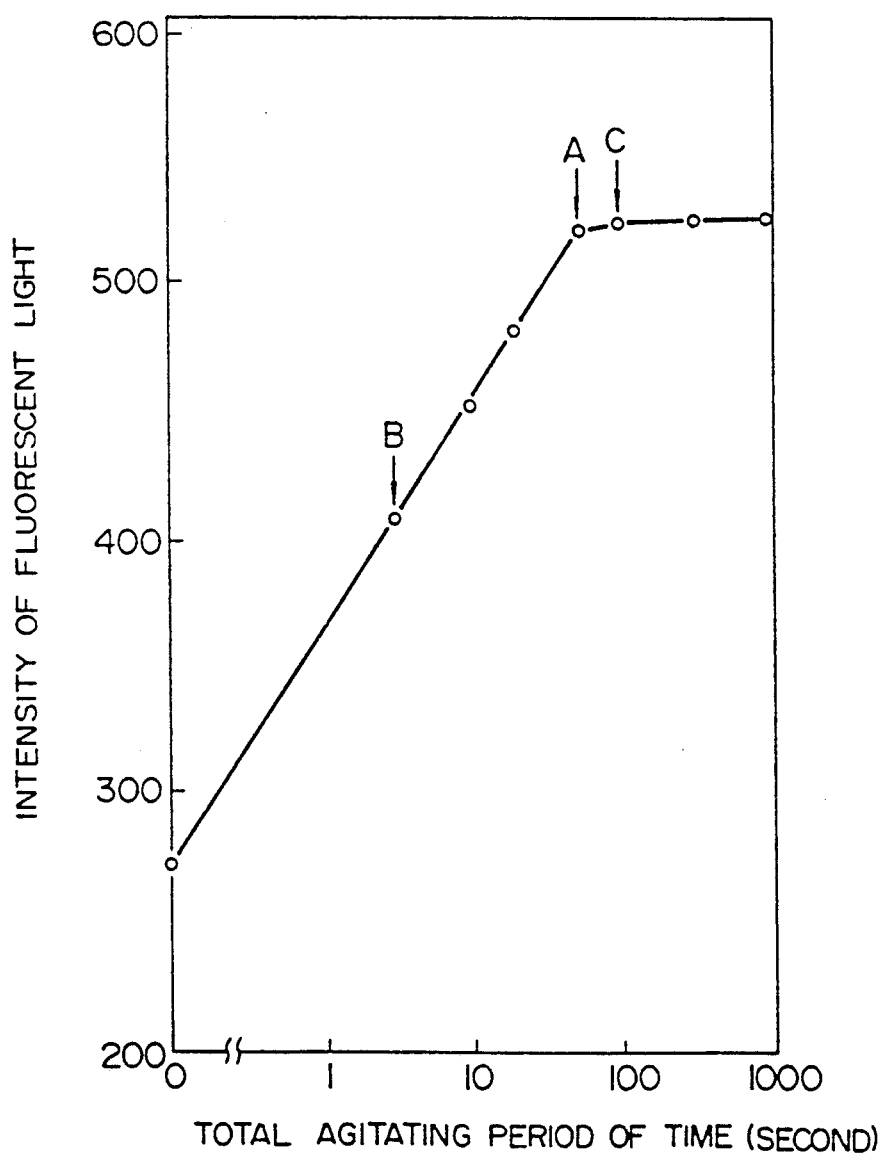
FIG. 5 is a graph showing the relationship between agitation time and fluorescent intensity.

FIG. 5 shows how the chemical reaction process is promoted by the agitation of the reaction solution. More specifically, in FIG. 5, the ordinate represents the intensity of fluorescent light produced as a result of the reaction between theophylline measuring reagents and 30 µg/ml of theophylline standard sample as in the case of later-mentioned Example 1, while the abscissa represents the total agitation time throughout the reaction period, i.e. from the moment at which the first reagent is added until the moment at which the photometry is executed.

Referring to FIG. 5, data point A has been obtained when the automatic analyzing apparatus of FIG. 2 was operated to cause 3-second agitation of the reaction solution after each 1-pitch feed of the reaction containers. Thus, data point A is the data point which has been obtained when the reaction solution is continuously and repeatedly agitated in the reaction process from the moment at which the reaction is started by the mixing of the sample and the reagent until the moment at which the photometry is executed. On the other hand, point B represents the data obtained with a conventional automatic analyzing device in which the reaction solution is agitated only once throughout the reaction.

From FIG. 5, it will be understood that the reaction proceeds to a higher degree as the frequency of agitation is increased, i.e., as the total agitation time is increased, so that the intensity of the fluorescent light produced as a result of the reaction is increased. In FIG. 5, point C represents data which has been obtained by a higher frequency of agitating operation than the frequency of agitating operation employed in the apparatus of the invention, i.e., the frequency at which the data point A is obtained.

It will be seen that data point A and C are almost at the same level of the fluorescent light intensity. This means that the effect of agitation is substantially saturated and no significant effect is produced even when the frequency of agitating operations is increased beyond the frequency adopted in the embodiment. This means that the operating condition which has produced the data point A is the condition which provides the highest efficiency of agitation. It is thus understood that the speed and degree of the reaction are largely influenced by the agitation of the reaction solution in the reaction process, and the reaction is remarkably promoted by continually agitating the reaction solution throughout the reaction period as in the case of the automatic analyzing apparatus of this embodiment.

In some cases, the reaction solution contains an insoluble component which can hardly be dispersed. In such cases, it is necessary that the reaction solution is frequently agitated so as to promote the reaction while avoiding precipitation. The agitation method employed in the apparatus of the embodiment is effective also in such cases.

In the present invention, the reaction container 2 may be beforehand charged with an agitation member such as an agitation ball. In such a case, the reaction container 2 is closed by various sealing membranes such as an aluminum film, polyethylene film or a silicone film. When such a sealing membrane is used, the apparatus may employ, separately from the pipetting probe, a seal breaker which can easily break the seal 5 so as to ensure that the pipetting can be executed without being hindered by the seal membrane 5. In such case, the seal 5 is broken by the seal breaker in advance of the pipetting. The arrangement, however, may be such that the seal membrane is broken by the pipetting probe 15 itself whenever the pipetting is to be executed.

The reaction container 2 is made of a suitable material such as a glass, plastic or the like which meets various requirements such as high strength, small adsorption of the reagent and sample, low production cost and, when the measurement is effected by means of photometry of the reaction solution in the reaction container 2, a high level of light transmissivity. An example of the material suitably used as the material of the reaction container 2 is an acrylic resin.

Although the agitation ball 4 used in this embodiment is made of permalloy, this is only illustrative and other materials can be used. In fact, it is considered that any material which has a specific gravity greater than the specific gravity of the solution to be agitated can be used as the material of the agitation ball. It is possible to enhance the agitation effect by varying the size of the agitation member depending on conditions such as the quantity and viscosity of the solution to be agitated. It is to be noted, however, that a surface treatment of the agitation ball such as plastic coating or plating is necessary when material which may soon become rusty or which chemically reacts with the solution, e.g., iron, is used as the material of the agitation member. When the measurement is conducted by direct photometry, it is preferred that the agitation ball is made of a ferromagnetic material such as permalloy or an iron so that the agitation ball can easily be attracted by an external magnet means so as to be held away from the path of the light beam 22. The use of a ferromagnetic material as the material of the agitation ball, however, involves the following problem regardless of whether it reacts with the reaction solution or not. Namely, when the reaction employs an iron-type catalyst, any residual magnetism on the agitation ball 4 tends to adversely affect the accuracy of the measurement. Therefore, in such a case, it is necessary that the material of the agitation ball exhibits only a small residual magnetism. Permalloy, which exhibits a low level of residual magnetism, can suitably be used in such cases where the accuracy of measurement is seriously affected by any residual magnetism. It is also preferred that the agitation member has a ball-like form as in the case of the described embodiment.

A description will be made hereinafter as to how the agitation efficiency is influenced by the factors such as the condition of high-speed reciprocating driving, configuration of the reaction container 2 and the configuration of the agitation member, with specific reference to FIGS. 6 and 7.

Figure 6:
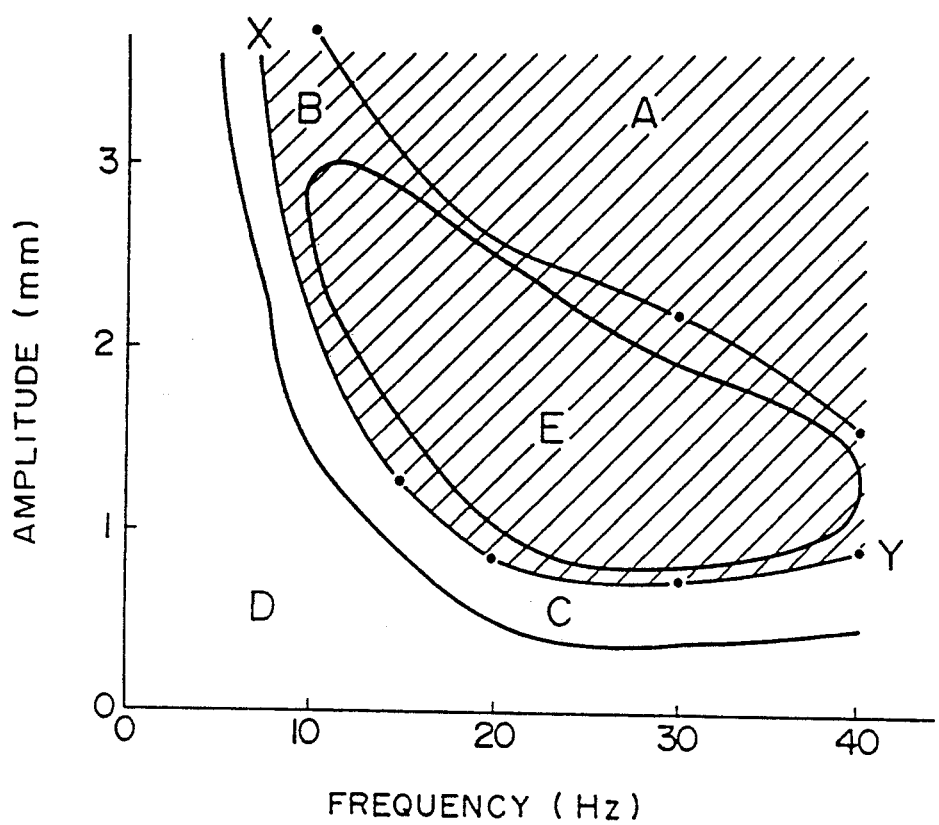
FIG. 6 is a graph illustrating vibration caused by high-speed reciprocatory movement.

In FIG. 6, the ordinate represents the amplitude of the high-speed reciprocatory driving, i.e., vibration, of the reaction disk, while the abscissa represents the frequency of the high-speed reciprocating driving. In this Figure, the regions of high-speed reciprocating driving which provide different levels of agitation efficiency are represented by A to E.

Figure 7:
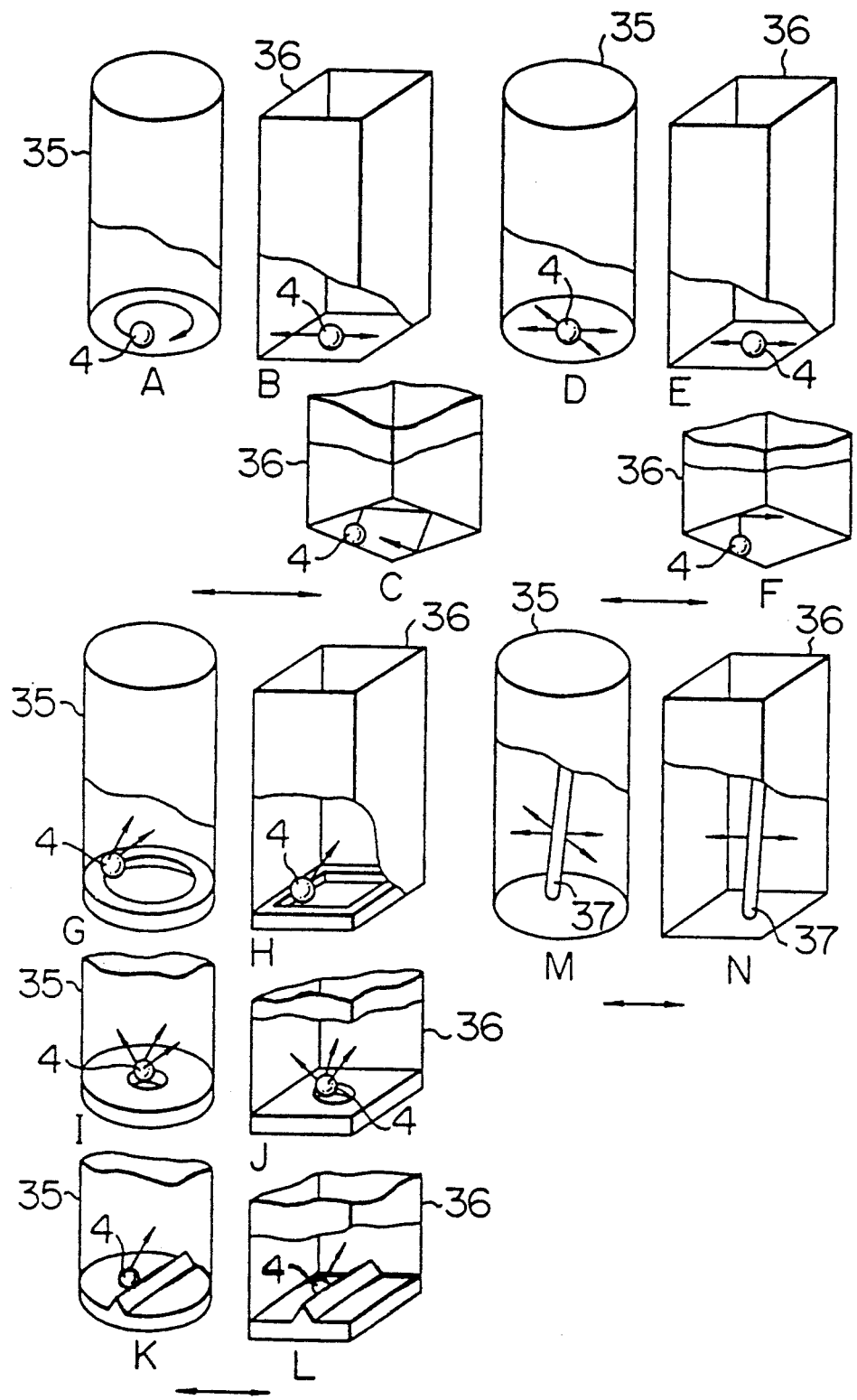
FIGS. 7A to 7N is an illustration of the behavior of the agitation member under the condition as shown in FIG. 6.

When the agitation member is a ball-shaped member as in the described embodiment, and when high-speed reciprocatory motion of large amplitude and high frequency is imparted to the cylindrical reaction container 35 as shown by A, B and E, the agitation ball 4 revolves along the inner peripheral surface of the cylindrical container 35 as shown at A in FIG. 7. This revolution of the agitation ball 4 enables the agitation to be completed within 3 seconds when the depth of the reaction solution is 10 times as large as the diameter of the agitation ball 4 or smaller. This agitation is caused by eddy currents in the solution. Thus, an agitation effect similar to that produced by a vortex mixer or a magnetic stirrer can be attained.

When the reaction container has a substantially rectangular cross-sectional form as shown in B of FIG. 7, the agitation can be effected only up to a depth which is 2 to 3 times as large as the diameter of the agitation ball 4 if the reaction container has a flat bottom, even when the condition of the high-speed reciprocatory motion is the same. However, if the high-speed reciprocatory motion takes place in the direction of a diagonal line of the container, the agitation ball 4 is caused to move two-dimensionally on the bottom of the container 36 as shown at C in FIG. 7 so that the agitation of the solution can be completed within about 5 seconds when the amount of the solution is up to 10 times as large as the diameter of the agitation ball 4 in terms of the depth.

When the reciprocatory motion of a frequency and amplitude falling within a region C in FIG. 6 is applied to a reaction container having a flat bottom, the above-mentioned revolution of the agitation ball along the wall of the cylindrical container 35 does not take place any more as shown at D in FIG. 7. As a consequence, a long agitation time of 3 to 20 seconds is required for completing the agitation when the depth of the solution is 10 times as large as the diameter of the agitation ball 4 or greater. Agitation is possible only up to a depth which is twice as large as the diameter of the agitation ball 4, if the high speed reciprocatory driving is effected in a direction parallel to one side of the rectangular cross section of the container 36. However, an agitation effect equivalent to that obtained with the cylindrical container can be produced when the container 36 having a rectangular cross-section is vibrated in a diagonal line of the cross-section of the container. When high-speed reciprocatory driving at a frequency and amplitude falling within the region D in FIG. 6 is imparted to a reaction container having a flat bottom, the agitation cannot be effected satisfactorily when the depth of the solution exceeds a value which is about twice as large as the diameter of the agitation ball 4. However, when the container has an annular step of a height substantially the same as the radius of the agitation ball on the bottom thereof along the inner peripheral surface as shown at G and H in FIG. 7, the agitation ball 4 is caused to move also in the vertical direction so that the agitation effect can be improved appreciably. Similar effect is obtained when the bottom of the container has a recess as shown at I and J in FIG. 7, a step or ridge as shown at K and L in FIG. 7 or other equivalent heightwise irregularity. Greater agitation effect is produced when the reaction container has a circular cross-section (G, I, K in FIG. 7) than when the reaction container has a rectangular cross-section (K, L in FIG. 7). This is attributable to the fact that the circular cross-section enables the agitation ball 4 to collide with the container wall at any angle between 0° and 90° so as to allow the ball to move in various directions when viewed in projection, as compared with the case of the rectangular cross-section in which the agitation ball always collides with the reaction vessel wall at 90°. However, an agitation effect substantially equivalent to that obtained with the cylindrical container 35 can be attained if the reaction container having the rectangular cross-section 36 is vibrated in an orthogonal direction to the cross-section.

In FIG. 7, M and N show two cases where a bar-shaped agitation member 37 is used. In this case, the solution can be agitated satisfactorily because the bar-shaped agitation member can move over a wide region of the solution. Although the bar-shaped agitation member provides a good agitation effect which well compares with that produced by the agitation ball 4, the use of the bar-shaped agitation member is not preferred from the view point of photometry.

The vertical movement of the agitation ball 4 caused by, for example, a step or recess in the bottom of the reaction container, as well as the use of the bar-shaped agitation member 37, is not preferred because in such a case the light-transmitting windows in the side wall of the reaction container may be damaged. Taking into account only the agitation effect, the regions A and B of frequency and amplitude shown in FIG. 6 are suitably employed. However, the frequency and amplitude in the region A tends to cause the reaction solution to splash out of the container because the agitation is effected too vigorously. Therefore, frequency and amplitude falling within the region B can suitably and practically be employed in the described embodiment.

If there is employed an amplitude of vibration, i.e., high-speed reciprocatory motion, greater than one step of intermittent rotation of the disk in a case of the direct photometric measurement during the vibration, the reaction vessel to be examined tends to fail to be aligned with the path of the measuring light beam to thereby make the measurement difficult. In addition, since the agitation member 4 of a ferromagnetic material is moved undesirably when the reaction vessel moves between a position where the external magnet 7 is located and the position where the agitation member 4 is free from the external magnet, the reaction solution is vigorously stirred to allow the liquid to foam or scatter. In order to eliminate such problems, therefore, the amplitude of the high-speed reciprocatory movement, i.e., the vibration, is preferably selected to be smaller than one pitch of the intermittent rotational movement of the reaction disk.

Referring to the agitating condition B in FIG. 6, the range of amplitude which can be suitably adopted is progressively narrowed as the frequency is increased. This means that the vibrating condition may undesirably be shifted from the optimum region B to another region which is undesirable, e.g., the region A, C or D, even by a slight fluctuation in the vibration amplitude on the order of, for example, less than one millimeter, caused by various reasons such as fluctuation in the state of meshing in the high-speed reciprocatory driving mechanism 3.

In view of these facts, it is understood that the condition of the high-speed reciprocatory driving, i.e., vibration, of the automatic analyzing apparatus of the invention preferably falls within a region E in FIG. 6, i.e., an amplitude which ranges between 0.8 and 3.0 mm and a frequency which ranges between 10 and 40 Hz.

Figure 8:
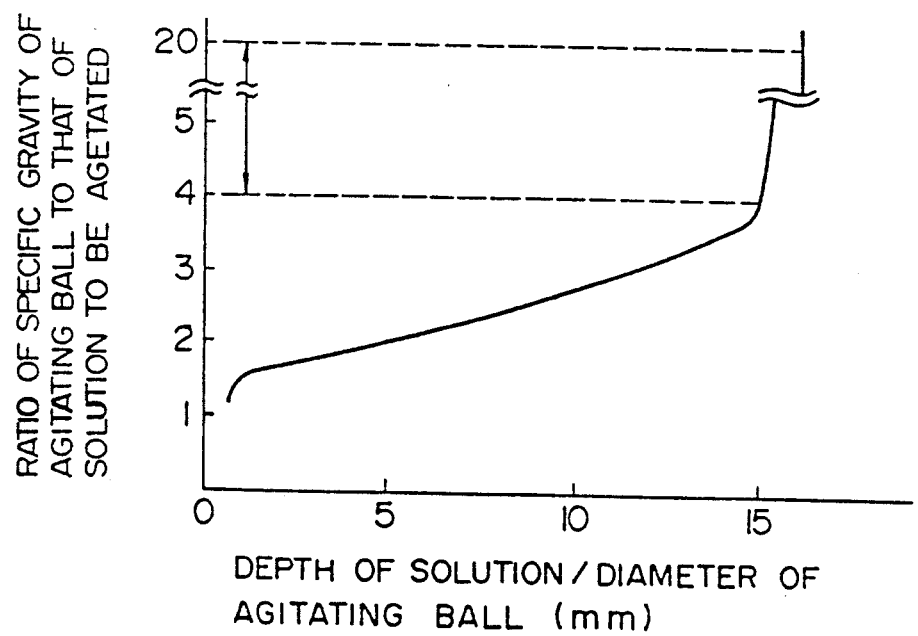
FIG. 8 is a graph showing the relationship between the quantity of solution agitatable and a ratio of the diameter of the agitation ball to the depth of solution.

FIG. 8 shows the relationship between the depth of the solution and the ratio of the specific gravity of the agitation ball to that of the solution to be agitated, which relation must be met in order to stir the solution in 3 seconds. More specifically, in FIG. 8, the ordinate represents the ratio of the specific gravity of the agitation ball to that of the solution to be agitated, while the abscissa represents the ratio of the solution depth to the diameter of the agitation ball.

For effecting the agitation satisfactorily in an agitation time which is about 3 seconds or so, the specific gravity of the agitation material must be increased as the specific gravity of the solution is increased. In a case of the agitation ball 4 shown in FIG. 1, the specific gravity of the agitation ball 4 must be about 1.5 times as large as that of the solution when the depth of the solution is about 4 times as large as the diameter of the agitation ball. When the ratio of the solution depth to the ball diameter exceeds 15, the agitation member must have a specific gravity which is about 4 times as large as that of the solution if the agitation is to be completed in 3 seconds. No further improvement in the agitation effect can be achieved even if the specific gravity of the agitation ball is increased beyond 4 times to the specific gravity of the solution. From these facts, it is understood that the agitation caused by vibratory motion of the reaction container 2 can be effected satisfactorily when the agitation ball 4 has a specific gravity which is not smaller than 1.5 times as that of the solution, preferably 4 times or more as large as the specific gravity of the solution to be agitated. The upper limit of the ratio of the specific gravity is practically about 20 or so because all inexpensive materials such as iron, copper, tungsten and so forth have a density which is not greater than 20 g/cm$^3$. This means that the practical range of the ratio of the specific gravity between the agitation member and the solution is between 4 and 20.

The inventors have found that the relationship between the diameter of the agitation ball and the diameter of cylindrical container which enables the agitation to be executed satisfactorily is expressed by the following formulas.

$$D \leq 4(A_2 + d), D \geq 1.1d \; (d < 10)$$

$$D \geq d + 1 \; (d \geq 10)$$

Where, $A_2$ is the total amplitude (sum of amplitudes in each direction from neutral position) expressed in terms of mm, while d and D respectively represent the diameter of the agitation ball and the inside diameter of the cylindrical container which also are expressed in terms of mm. Considering that the diameter of reaction container usually employed in automatic analysis does not exceed 30 mm, it is understood that the agitation can be executed satisfactorily when the following condition is met if the total amplitude $A_2$ is not smaller than 7.5 mm ($A_2 \geq 7.5$):

$$1.48 \, d \leq D \leq 4.4 \, d \; (A_2 \geq 7.5)$$

When the total amplitude $A_2$ is below 7.5 mm, the agitation is effected satisfactorily when the vibrating condition falls within a triangular zone which is defined by interconnecting the three coordinate points of (0.909$A_2$, 4$A_2$), (2.73$A_2$, 4$A_2$) and (0,0), as well as within a trapezoidal zone which is formed by interconnecting the following four points: namely, (0.909$A_2$, 4$A_2$), (2.73$A_2$, 4$A_2$), (22.2−0.25A, 30), (12.5−0.75$A_2$, 30) and ((0.909$A_2$, 4$A_2$)).

Figure 9:
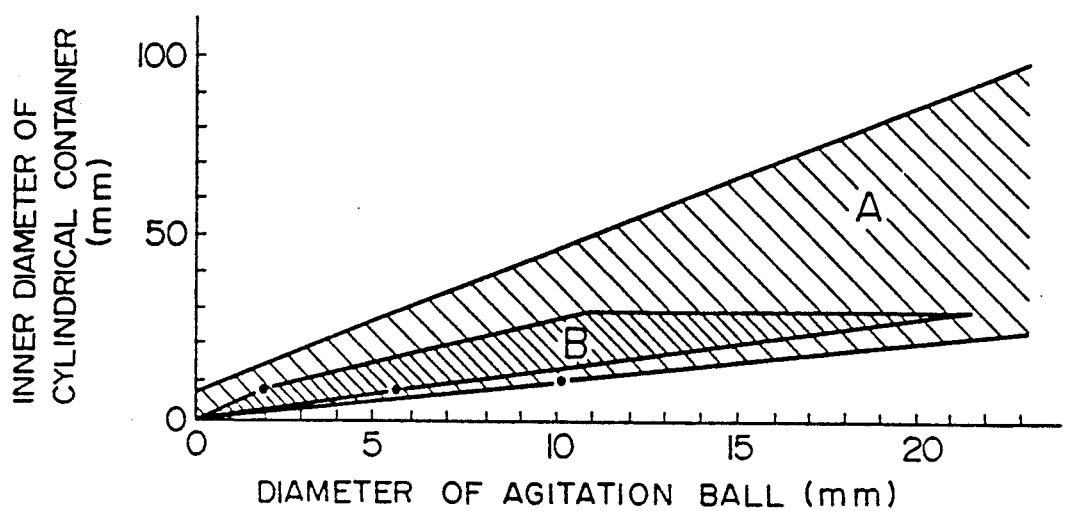
FIG. 9 is a graph showing the relationship between the diameter of the agitation ball and the inside diameter of cylindrical reaction container suitable for agitation as obtained when total vibration amplitude is 2 mm.

FIG. 9 shows the relationship between the diameters D and d which provides satisfactory agitation by vibration at total amplitude of 2 mm. In FIG. 9, the ordinate represents the inside diameter D (mm) of the cylindrical container, while the axis of abscissa represents the ball diameter d (mm). In FIG. 9, A represents the region in which the agitation is possible while B shows the region suitable particularly for the automatic analysing apparatus.

Figure 11:
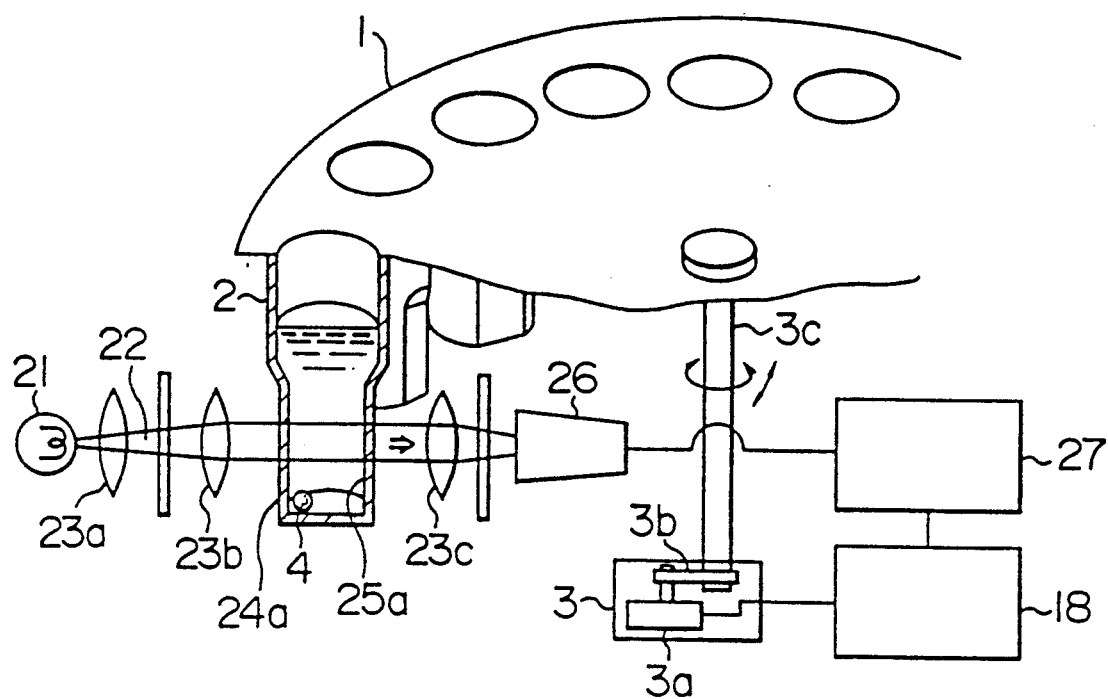
FIG. 11 is a schematic illustration of another embodiment of the present invention.
Figure 12:
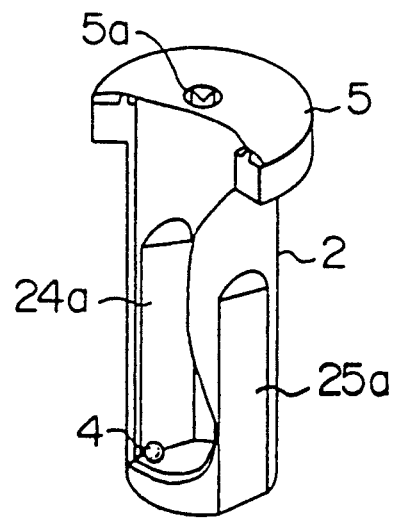
FIG. 12 is an illustration of a reaction container suitable for use in a direct light-absorption type measurement.
Figure 13A:
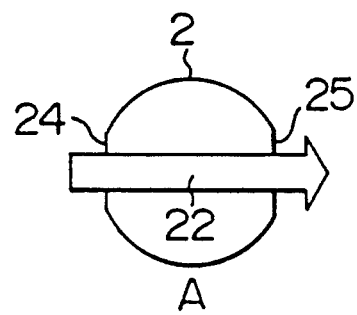
FIGS. 13A to 13C are schematic illustrations of various modifications of the reaction container.
Figure 13B:
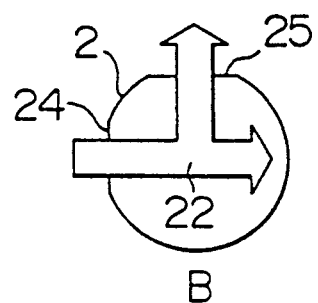
Figure 13C:
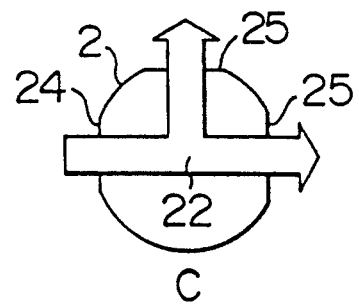

FIG. 11 illustrates the arrangement of an embodiment in which a light-transmission characteristic of the reaction solution is measured by making use of the reaction container 2a of the type shown in FIG. 12. In this Figure, the same reference numerals are used to denote the same parts or members as those used in the embodiment shown in FIG. 1. Referring to FIG. 12, an incident window 24a and a window 25a for outgoing light which are parallel to each other are formed in the wall of the reaction container 2a. When the light transmissivity is measured, the agitation member 4 is seated on the bottom of the reaction container 4. The measuring device is so arranged that the light runs along a path which is set above the position of the agitation member 4 seated on the bottom of the container, so that the measurement of the light transmissivity is effected without any problem. In this embodiment, it is not essential that the agitation member 4 is made of a ferromagnetic material. Thus, the agitation member 4 is made of any suitable material such as aluminum, copper or other metal regardless of whether it is ferromagnetic or not, as well as other non-magnetic material such as glass. It is also possible to use an agitation member made of a magnet. FIGS. 13A to 13C show various forms of the reaction containers. In each case, a plurality of light-transmitting windows are formed in the side wall of the container. For instance, FIG. 13A shows a substantially cylindrical reaction container in which a pair of light-transmitting windows are formed in two opposing walls. This type of reaction container is suitable for light-absorption type measurement. FIG. 13B shows a substantially cylindrical reaction container which is provided with light-transmitting windows arranged such that their optical axes orthogonally intersect each other. This type of reaction container is suitable for use in fluorescent measurement. A reaction container of FIG. 13C, which is provided with three light-transmitting windows arranged at 90° interval, is suitable for use both in light-absorption type measurement and fluorescent measurement.

EXAMPLE 1

By using the automatic analyzing apparatus of FIG. 1, an analysis of theophylline was executed to thereby obtain the following results.

An AIMS TDM TM theophylline kit, available from Miles Sankyo Kabushiki Kaisha was used as the reagent. Reaction containers 11 set on the sample disk 8 were charged with theophylline standard solutions (0, 10, 20, 30 and 40 µg/ml). Theophylline measuring reagents, including $\beta$-galactisydaze and theophylline antibody as the first reagent and a fluorescent reference theophylline ($\beta$-galactosyl-umbelkliferone-theophylline) were used as a second reagent.

Figure 10:
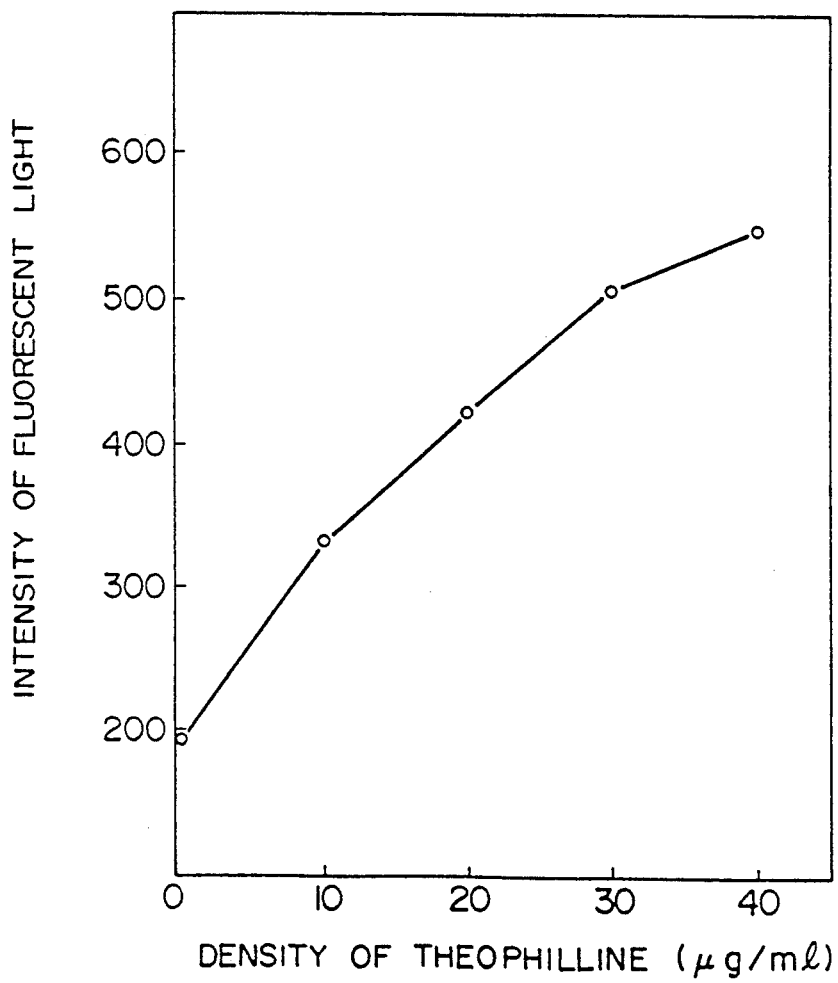
FIG. 10 is a graph showing theophylline standard curve as obtained through measurement by the apparatus shown in FIG. 2.

50 µl of each sample was mixed with 250 µl of the first reagent so as to react with the first reagent for a period of 36 minutes. Then, 50 µl of the second reagent were added to the reaction solution and, at a moment 5 minutes after the addition of the second reagent, light of an exciting wavelength of 400 nm was applied and measurement was conducted at a fluorescent wavelength of 450 nm. FIG. 10 shows a calibration curve in which the density of theophylline standard solutions and the measured fluorescent intensities are plotted on the abscissa and the ordinate, respectively.

What is claimed is:

1. A method for the automatic analysis of a reaction solution, comprising the steps of:
    providing a plurality of reaction containers on a reaction disk;
    providing an agitation member made of a ferromagnetic material in each reaction container;
    supplying a reaction solution in each of said reaction containers;
    driving said reaction disk in intermittent rotational movement and in reciprocating rotational movement to vibrate said reaction disk for a predetermined period of time for moving said agitation members, and for thereby agitating the reaction solutions contained in the reaction containers; and
    photometrically measuring a reaction solution in one of said reaction containers while magnetically attracting the agitation member in the reaction container under measurement towards a wall of the reaction container to prevent the agitation member from interfering with the photometric measurement.

2. A method for the automatic analysis of a reaction solution as claimed in claim 1, wherein said step of driving said reaction disk vibrates said reaction disk with an amplitude that is smaller than a distance between two adjacent reaction containers disposed on the reaction disk such that the agitation member in each said reaction container circulates along an inner surface of the wall of the reaction container to thereby rotate the reaction solution contained therein.

3. A method for the automatic analysis of a reaction solution as claimed in claim 1, wherein said step of providing a plurality of reaction containers includes the step of providing each said reaction container with a substantially cylindrical shape and a substantially flat light-transmitting window for allowing passage of a light beam therethrough during said step of photometric measurement.

4. A method for the automatic analysis of a reaction solution as claimed in claim 1, further comprising the step of mounting the reaction disk for rotation on a shaft, wherein said step of driving said reaction disk is carried out by rotating said shaft in one of two different operational mode steps, said two different operational mode steps comprising said intermittent rotational movement and said reciprocating rotational movement.

5. A method for the automatic analysis of a reaction solution, comprising the steps of:
    providing a reaction disk on which a plurality of reaction containers are arranged, each said reaction container being provided with an agitation ball;
    supplying a sample and a reagent into each of said reaction containers to form a reaction solution in each of said reaction containers; and
    reciprocatingly driving said reaction disk in reciprocating rotational movement of a predetermined amplitude to provide an arcuate vibrational movement to said reaction disk so as to move each said agitation ball to agitate the reaction solution in its respective reaction container.

6. A method for the automatic analysis of a reaction solution as claimed in claim 5, wherein said step of driving provides the vibrational movement to said reaction containers at an arcuate amplitude of 0.8 to 3.0 mm and a frequency of 10 to 40 Hz.

7. A method for the automatic analysis of a reaction solution as claimed in claim 5, wherein the step of providing a reaction disk is carried out so that each said agitation ball has a specific gravity of at least four times as large as the specific gravity of a reaction solution contained in the same reaction container as the agitation ball.

8. A method for the automatic analysis of a reaction solution as claimed in claim 5, wherein the step of providing a reaction container includes the step of providing each said reaction container to have an inside diameter of 1.5 to 4.4 times as large as the diameter of the corresponding agitation ball.

9. A method for the automatic analysis of a reaction solution as claimed in claim 6, wherein said step of providing a reaction container is carried out to provide a reaction container having a substantially cylindrical shape and a substantially flat light-transmitting window for allowing passage of a light beam therethrough during the step of photometrically measuring a reaction solution.

10. A method for the automatic analysis of a reaction solution as claimed in claim 5, wherein the step of providing an agitation ball is carried out to provide an agitation ball made of permalloy.

11. A method for the automatic analysis of a reaction solution as claimed in claim 5, wherein the step of providing an agitation ball is carried out so that each said agitation ball is coated with a corrosion-resistant material.

12. A method for the automatic analysis of a reaction solution as claimed in claim 5, further comprising the step of providing a photometer disposed in a photometric measuring position adjacent to said reaction disk so that the photometric measuring step is effected for a reaction solution contained in a reaction container brought to said photometric measuring position.

13. A method for the automatic analysis of a reaction solution as claimed in claim 12, wherein said step of providing a photometer is carried out to provide a fluorescent photometer, and said method further comprises the steps of applying an exciting light beam from said fluorescent photometer to said reaction container at said photometric measuring position from a first wall portion of said reaction container, and detecting fluorescent light emanating from a second wall portion of said reaction container.

14. A method for the automatic analysis of a reaction solution as claimed in claim 13, wherein said step of providing a reaction container is carried out to provide a reaction container having a substantially cylindrical shape and a substantially flat light-transmitting window for allowing passage of a light beam therethrough.

15. A method for the automatic analysis of a reaction solution as claimed in claim 13, wherein said step of providing a reaction container is carried out so that the first wall portion of the reaction container is located at a lower portion of said reaction container, and the second wall portion of said reaction container is located at a lateral side of said reaction container.

16. A method for the automatic analysis of a reaction solution as claimed in claim 12, further comprising the step of magnetically attracting said agitation ball towards the wall of said reaction container at said photometric measuring position and out of the photometric measurement light path.

17. A method for the automatic analysis of a reaction solution as claimed in claim 5, wherein said step of driving is carried out to drive said reaction disk in an arcuate vibrational movement with an amplitude that is smaller than a distance between two adjacent reaction containers disposed on the reaction disk such that the agitation ball in each reaction container circulates along an inner surface of a wall of the reaction container to thereby rotate a reaction solution contained therein.

18. A method for the automatic analysis of a reaction solution as claimed in claim 5, further comprising the step of mounting a reaction disk for rotation on a shaft, and wherein said driving step is carried out to drive said shaft in a reciprocating rotational movement, and in an intermittent rotational movement to position said reaction containers in one of a plurality of predetermined positions.

19. A method for the automatic analysis of a reaction solution, comprising the steps of:
  providing a plurality of reaction containers;
  providing an agitation member within each said reaction container, said agitation member being made of a magnetic material;
  providing a rotatable reaction disk upon which each said reaction container is arranged;
  supplying at least one of a reagent and a sample to one of said reaction containers at a predetermined position while the reaction disk is stationary;
  reciprocatingly moving said reaction disk in rotation for a predetermined period for moving said agitation member in each said reaction container to agitate the reaction solution contained therein;
  effecting a stepwise rotative movement of said reaction disk following cessation of said reciprocating movement; and
  photometrically measuring a reaction solution in a reaction container.

20. A method for the automatic analysis of a reaction solution as claimed in claim 19, wherein said step of driving is carried out to vibrate said reaction disk in reciprocating rotation with an amplitude that is smaller than a distance between two adjacent reaction containers disposed on the reaction disk such that the agitation member in each said reaction container circulates along an inner surface of a wall of the reaction container to thereby rotate a reaction solution contained therein.

21. A method for the automatic analysis of a reaction solution as claimed in claim 20, wherein said step of providing a reaction disk is carried out by mounting said reaction disk for rotation on a shaft, and wherein said step of driving is carried out to drive said shaft in a stepwise manner.

22. A method for the automatic analysis of a reaction solution as claimed in claim 19, wherein said step of providing a reaction container is carried out to provide a reaction container having a substantially cylindrical shape and a substantially flat light-transmitting window for allowing passage of a light beam emitted from the photometric means therethrough.

* * * * *